(12) United States Patent
Arp et al.

(10) Patent No.: US 11,642,475 B2
(45) Date of Patent: *May 9, 2023

(54) DRY POWDER INHALER

(71) Applicant: PHARMACHEMIE B.V., Haarlem (NL)

(72) Inventors: Jan Arp, Haarlem (NL); Johan Keegstra, Haarlem (NL); Michael Imre Goller, Haarlem (NL)

(73) Assignee: PHARMACHEMIE B.V., Haarlem (NL)

(*) Notice: Subject to any disclaimer, the term of this patent is extended or adjusted under 35 U.S.C. 154(b) by 71 days.

This patent is subject to a terminal disclaimer.

(21) Appl. No.: 17/333,307

(22) Filed: May 28, 2021

(65) Prior Publication Data
US 2021/0353881 A1    Nov. 18, 2021

Related U.S. Application Data

(63) Continuation of application No. 15/101,689, filed as application No. PCT/EP2014/075043 on Nov. 19, 2014, now Pat. No. 11,020,546.

(30) Foreign Application Priority Data

Dec. 9, 2013  (GB) .................................. 1321712

(51) Int. Cl.
*A61M 15/00* (2006.01)
*A61K 9/00* (2006.01)
(Continued)

(52) U.S. Cl.
CPC ....... *A61M 15/0008* (2014.02); *A61K 9/0075* (2013.01); *A61K 31/167* (2013.01);
(Continued)

(58) Field of Classification Search
CPC .......... A61M 15/0008; A61M 15/0021; A61M 15/0065; A61M 15/0086;
(Continued)

(56) References Cited

U.S. PATENT DOCUMENTS

| 5,674,860 A | 10/1997 | Carling et al. |
| 7,759,328 B2 | 7/2010 | Govind et al. |

(Continued)

FOREIGN PATENT DOCUMENTS

| EP | 3079744 | 10/2016 |
| JP | 3342484 B2 | 8/2002 |

(Continued)

OTHER PUBLICATIONS

Great Britain Application No. GB1417412.2, filed Oct. 1, 2014.
Great Britain Applicaton No. 1319265.3, filed Oct. 31, 2013.

*Primary Examiner* — Rachel T Sippel
(74) *Attorney, Agent, or Firm* — BakerHostetler

(57) ABSTRACT

This invention provides a budesonide/formoterol dry powder inhaler (10) comprising:
  a reservoir (14) containing a dry powder medicament and an arrangement for delivering a metered dose of the medicament from the reservoir;
  a cyclone deagglomerator (10') for breaking up agglomerates of the dry powder medicament;
  a delivery passageway (34) for directing an inhalation-induced air flow through a mouthpiece (24), the delivery passageway extending to the metered dose of medicament,
wherein the medicament comprises micronised formoterol fumarate, micronised budesonide and a lactose carrier, the lactose carrier having a particle size distribution of d10=20-65 μm, d50=80-120 μm, d90=130-180 μm and <10 μm=<10%.

13 Claims, 16 Drawing Sheets

(51) Int. Cl.
*A61K 31/167* (2006.01)
*A61K 31/58* (2006.01)

(52) U.S. Cl.
CPC .......... *A61K 31/58* (2013.01); *A61M 15/0021* (2014.02); *A61M 15/0065* (2013.01); *A61M 15/0086* (2013.01); *A61M 2202/064* (2013.01); *A61M 2206/16* (2013.01)

(58) Field of Classification Search
CPC ........ A61M 2202/064; A61M 2206/16; A61K 9/0075; A61K 31/167; A61K 31/58
See application file for complete search history.

(56) References Cited

U.S. PATENT DOCUMENTS

| | | | |
|---|---|---|---|
| 7,897,646 B2 | 3/2011 | Bauer et al. | |
| 8,143,239 B2 | 3/2012 | Govind et al. | |
| 8,461,211 B2 | 6/2013 | Bauer et al. | |
| 8,575,137 B2 | 11/2013 | Govind et al. | |
| 2002/0078950 A1 | 6/2002 | O'Leary | |
| 2002/0088463 A1 | 7/2002 | Keane et al. | |
| 2010/0065048 A1 | 3/2010 | Mueller-Walz et al. | |
| 2010/0291221 A1 | 11/2010 | Cook et al. | |
| 2011/0108030 A1 | 5/2011 | Blair et al. | |
| 2013/0202778 A1 | 8/2013 | Bilgic | |
| 2013/0319411 A1 | 12/2013 | Weers et al. | |
| 2016/0271345 A1 | 9/2016 | Blair et al. | |

FOREIGN PATENT DOCUMENTS

| | | |
|---|---|---|
| JP | 2013-091316 A | 5/2013 |
| WO | 93/11773 A1 | 6/1993 |
| WO | 2009/158300 A1 | 12/2009 |
| WO | 2011/049539 A1 | 4/2011 |
| WO | 2011/093817 A1 | 8/2011 |
| WO | 2015/086276 A1 | 6/2015 |

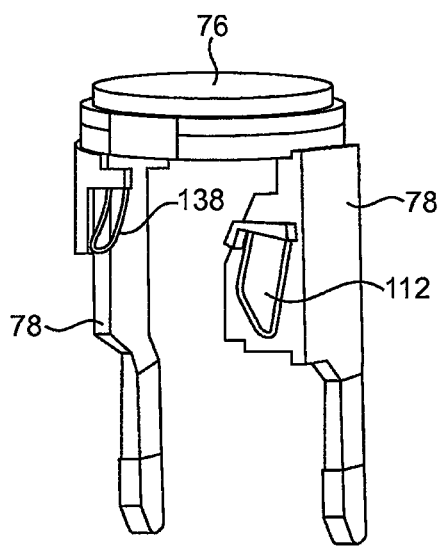 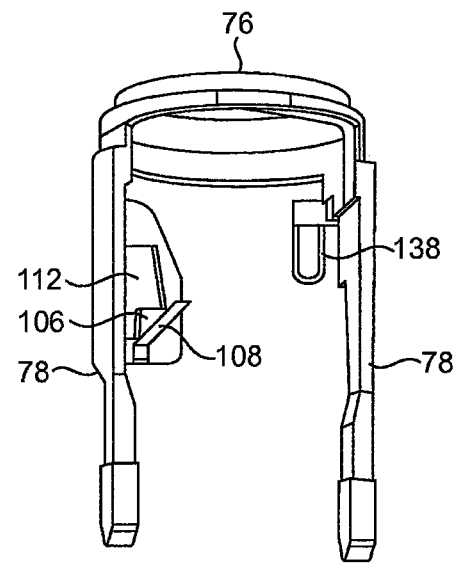
FIG. 11    FIG. 12
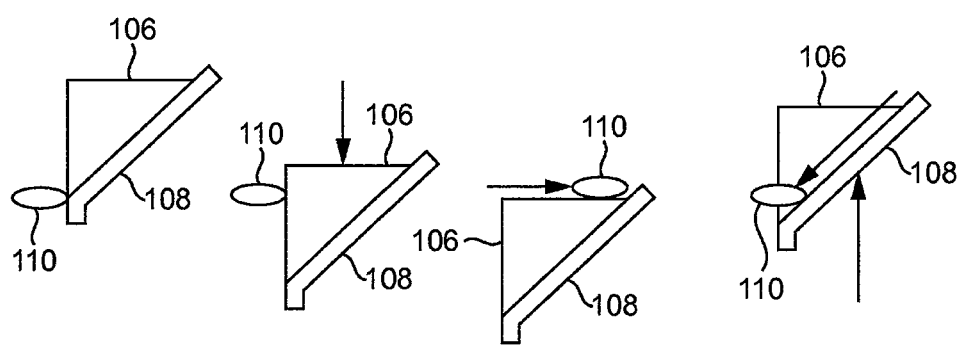
FIG. 13

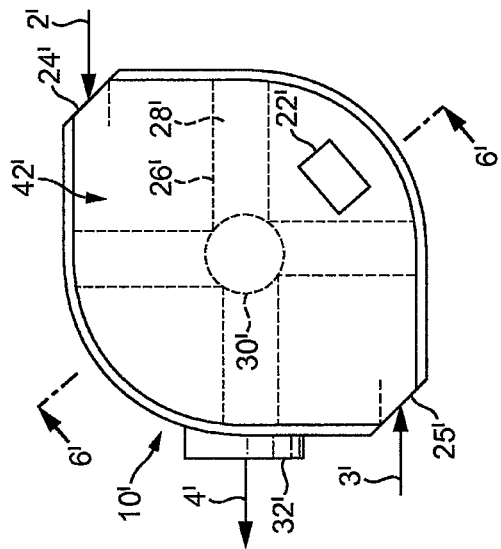
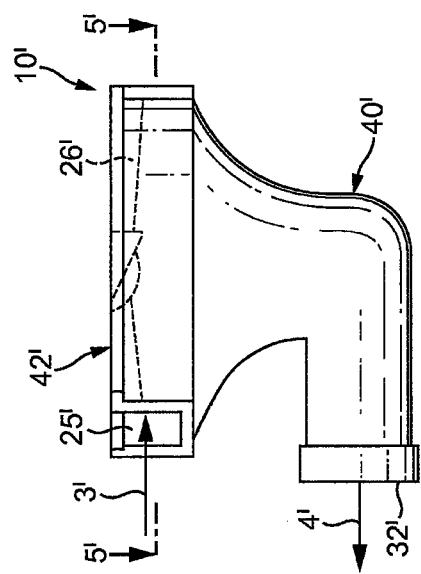
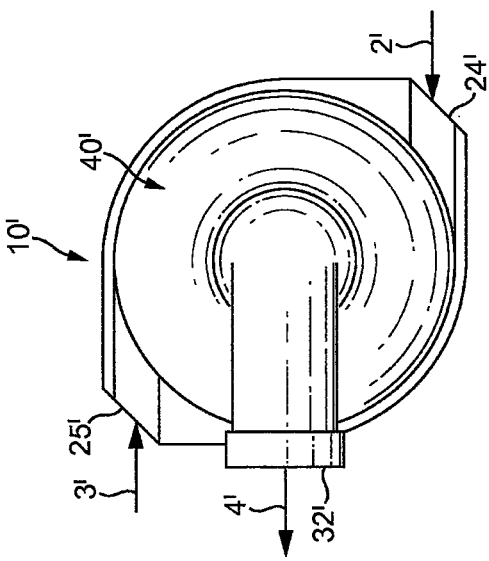
FIG. 19
FIG. 20
FIG. 18

DRY POWDER INHALER

CROSS-REFERENCE TO RELATED APPLICATIONS

This application is a continuation of U.S. patent application Ser. No. 15/101,689, filed Jun. 3, 2016, which is the U.S. National Stage of International Application No. PCT/EP2014/075043, filed Nov. 19, 2014, which claims the benefit of Great Britain application number 1321712.0, filed Dec. 9, 2013. The disclosures of each of the aforementioned applications is incorporated herein by reference in its entirety.

The present invention relates to a dry powder inhaler, and particularly to a dry powder inhaler containing a combination of budesonide and formoterol.

Budesonide is a corticosteroid indicated for the treatment of asthma and COPD. Formoterol is a long-acting $\beta_2$-adrenergic receptor agonist that is also indicated for the treatment of asthma and COPD. Formoterol is typically administered as the fumarate salt.

Combination therapy with budesonide and formoterol fumarate ("BF") is commonly used to treat asthma and COPD. The active ingredients may be administered separately or in a fixed dose combination. The usual approaches for formulating inhalable medicaments are using a dry powder inhaler (DPI), pressurised metered dose inhaler (pMDI) or nebuliser.

In the case of DPIs, it is important to balance the flow properties of the dry powder within the inhaler and the plume characteristics on inhalation. Coarse carrier particles, usually lactose, are used to aid the flow properties of the medicament, but it is important to ensure that the active ingredients separate from the coarse carrier on inhalation so that the fine particles of the active ingredients are entrained into the lungs. To provide an appropriate dose over the lifetime of the inhaler, it is important that this process occurs in a consistent manner. That is, inhalation devices must demonstrate a consistent delivered dose and fine particle mass from the first to the last dose. The EU Pharmacopeia compendial procedure specifies that 9 out of 10 DPI doses are within ±25% of the specified dose and that outliers should be within ±35% (Preparations for inhalation 01/2012: 671 in the European Pharmacopoeia, 8th Edition. Council of Europe, 2013).

Thus, there is a requirement in the art for a BF DPI which provides a consistent delivered dose and fine particle mass over the lifetime of the inhaler.

Accordingly, the present invention provides a budesonide/formoterol dry powder inhaler comprising:

a reservoir containing a dry powder medicament and an arrangement for delivering a metered dose of the medicament from the reservoir;

a cyclone deagglomerator for breaking up agglomerates of the dry powder medicament;

a delivery passageway for directing an inhalation-induced air flow through a mouthpiece, the delivery passageway extending to the metered dose of medicament, wherein the medicament comprises micronised formoterol fumarate, micronised budesonide and a lactose carrier, the lactose carrier having a particle size distribution of d10=20-65 µm, d50=80-120 µm, d90=130-180 µm and <10 µm=<10%.

The present invention will now be described with reference to the drawings, in which:

FIG. 11 is a second side isometric view of the yoke of the inhaler of FIG. 1;

FIG. 12 is a first side isometric view of the yoke of the inhaler of FIG. 1, showing a ratchet and a push bar of the yoke;

FIG. 13 is a schematic illustration of lateral movement of a boss of the medicament cup in response to longitudinal movement of the ratchet and the push bar of the yoke of the inhaler of FIG. 1;

FIG. 18 is a side elevation view of the deagglomerator of FIG. 17;

FIG. 19 is a top plan view of the deagglomerator of FIG. 17;

FIG. 20 is a bottom plan view of the deagglomerator of FIG. 17;

Figure 24:
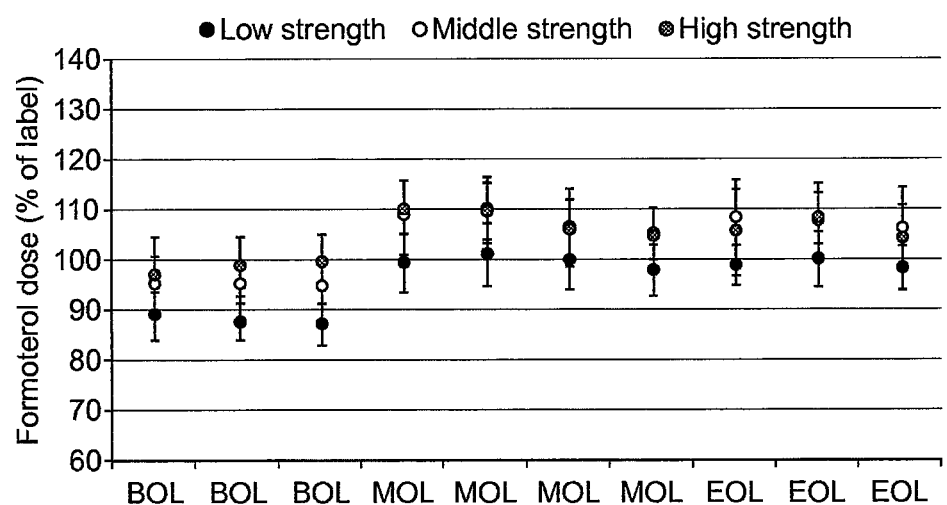
Figure 25:
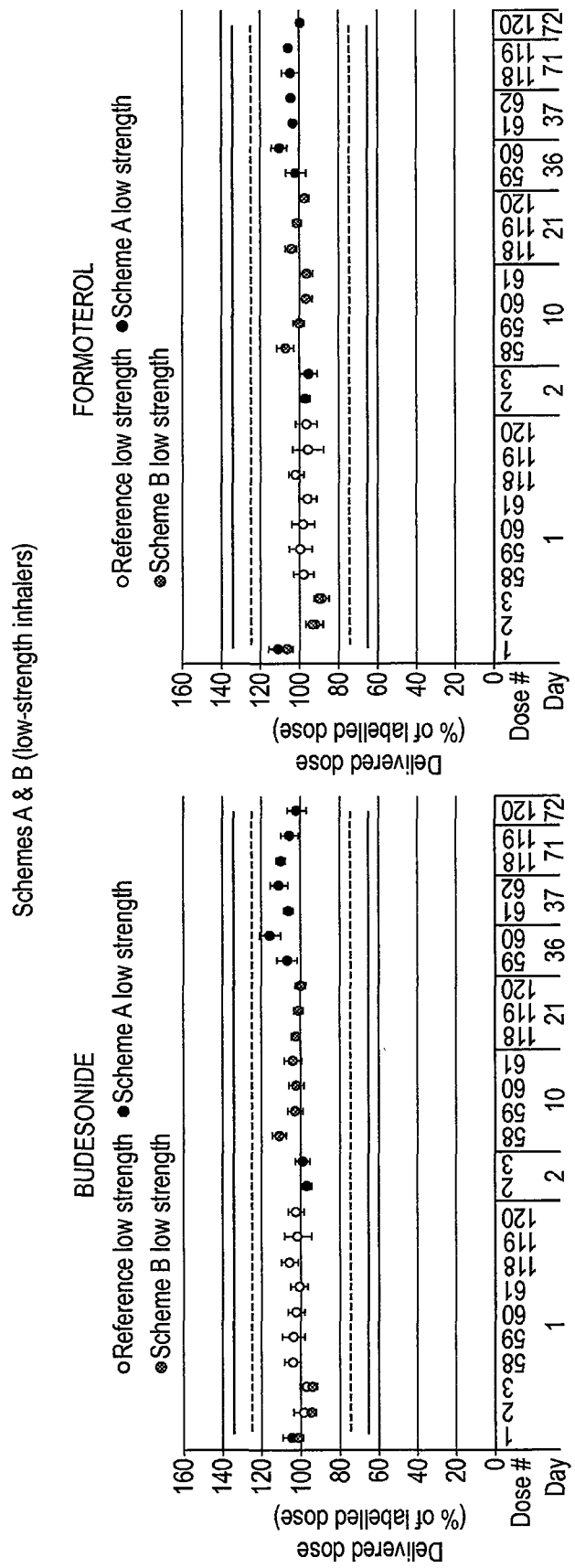
Figure 25:
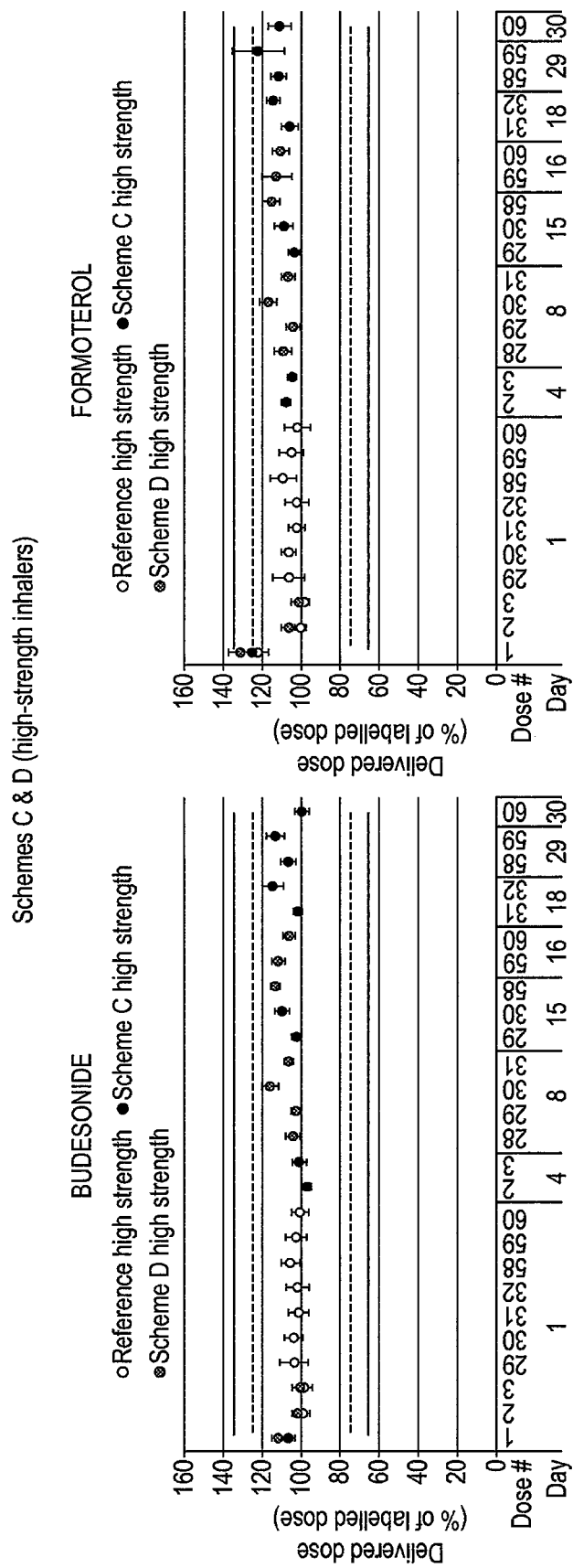
Figure 25:
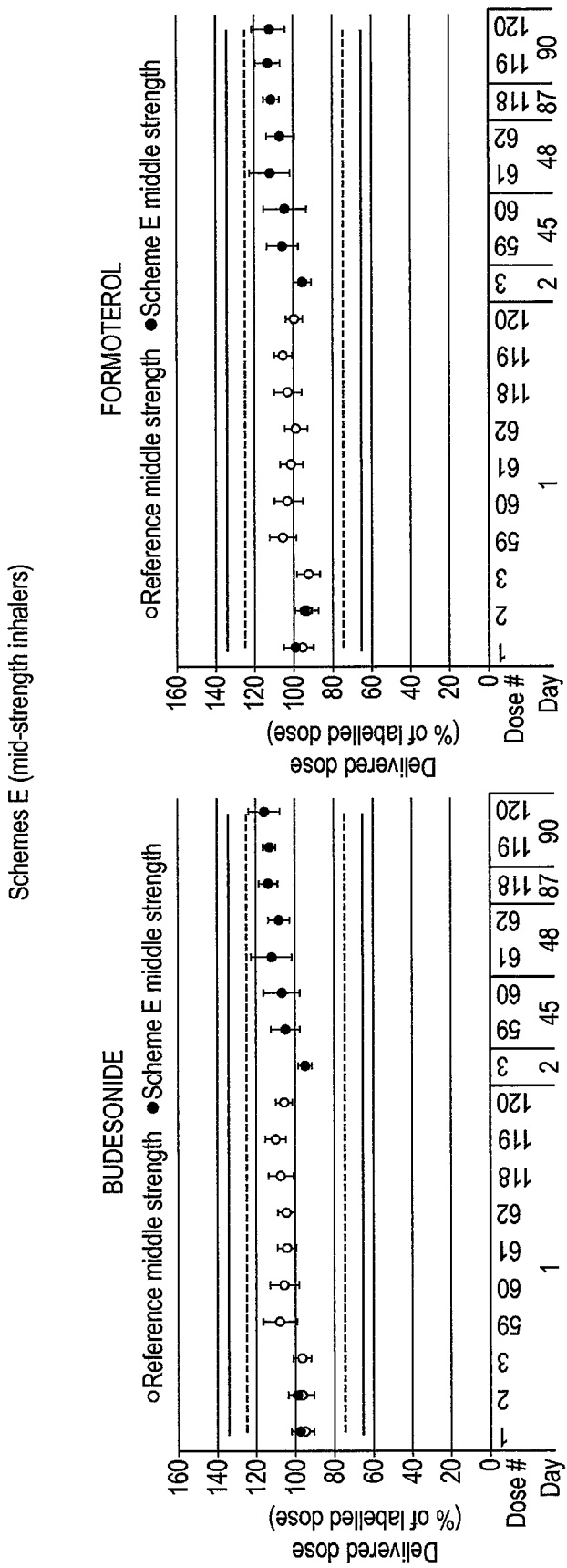

FIG. 24 shows the delivered dose (DD) of formoterol by low, middle and high strength BF Spiromax inhalers at BOL, MOL and EOL of each device (error bars represent standard deviation and data are presented as percentage of the labeled dose); and FIG. 25 shows doses delivered by BF Spiromax: low strength inhaler (simulation schemes A & B), high strength inhaler (simulation schemes C & D and middle strength inhaler (simulation scheme E), with data presented as percentage of the labeled dose.

The inhaler of the present invention includes: a reservoir containing a dry powder medicament and an arrangement for delivering a metered dose of the medicament from the reservoir; a cyclone deagglomerator for breaking up agglomerates of the dry powder medicament; a delivery passageway for directing an inhalation-induced air flow through a mouthpiece, extending to the metered dose of medicament.

In a preferred form, the dose metering system includes a cup received in the channel, which is movable between the dispenser port and the delivery passageway, a cup spring biasing the cup towards one of the dispenser port and the passageway, and a yoke movable between at least two positions. The yoke includes a ratchet engaging the cup and preventing movement of the cup when the yoke is in one of the positions, and allowing movement of the cup when the yoke is in another of the positions.

The inhaler includes a cyclone deagglomerator for breaking up agglomerates of the active ingredients and carrier. This occurs prior to inhalation of the powder by a patient. The deagglomerator includes an inner wall defining a swirl chamber extending along an axis from a first end to a second end, a dry powder supply port, an inlet port, and an outlet port.

The supply port is in the first end of the swirl chamber for providing fluid communication between a dry powder delivery passageway of the inhaler and the first end of the swirl chamber. The inlet port is in the inner wall of the swirl chamber adjacent to the first end of the swirl chamber and provides fluid communication between a region exterior to the deagglomerator and the swirl chamber. The outlet port provides fluid communication between the second end of the swirl chamber and a region exterior to the deagglomerator.

A breath-induced low pressure at the outlet port causes air flows into the swirl chamber through the dry powder supply port and the inlet port. The air flows collide with each other and with the wall of the swirl chamber prior to exiting through the outlet port, such that the active is detached from the carrier (lactose). The deagglomerator further includes vanes at the first end of the swirl chamber for creating additional collisions and impacts of entrained powder.

A first breath-actuated air flow is directed for entraining a dry powder from an inhaler into a first end of a chamber extending longitudinally between the first end and a second end, the first air flow directed in a longitudinal direction.

A second breath-actuated airflow is directed in a substantially transverse direction into the first end of the chamber such that the air flows collide and substantially combine.

Then, a portion of the combined air flows is deflected in a substantially longitudinal direction towards a second end of the chamber, and a remaining portion of the combined air flows is directed in a spiral path towards the second end of the chamber. All the combined air flows and any dry powder entrained therein are then delivered from the second end of the chamber to a patient's mouth.

The deagglomerator ensures that particles of the actives are small enough for adequate penetration of the powder into a bronchial region of a patient's lungs during inhalation by the patient.

Thus, in an embodiment of the present invention, the deagglomerator comprises: an inner wall defining a swirl chamber extending along an axis from a first end to a second end; a dry powder supply port in the first end of the swirl chamber for providing fluid communication between a dry powder delivery passageway of the inhaler and the first end of the swirl chamber; at least one inlet port in the inner wall of the swirl chamber adjacent to the first end of the swirl chamber providing fluid communication between a region exterior to the deagglomerator and the first end of the swirl chamber; an outlet port providing fluid communication between the second end of the swirl chamber and a region exterior to the deagglomerator; and vanes at the first end of the swirl chamber extending at least in part radially outwardly from the axis of the chamber, each of the vanes having an oblique surface facing at least in part in a direction transverse to the axis; whereby a breath-induced low pressure at the outlet port causes air flows into the swirl chamber through the dry powder supply port and the inlet port.

The inhaler has a reservoir for containing the medicament and an arrangement for delivering a metered dose of the medicament from the reservoir. The reservoir is typically a pressure system. The inhaler preferably includes: a sealed reservoir including a dispensing port; a channel communicating with the dispensing port and including a pressure relief port; a conduit providing fluid communication between an interior of the sealed reservoir and the pressure relief port of the channel; and a cup assembly movably received in the channel and including, a recess adapted to receive medicament when aligned with the dispensing port, a first sealing surface adapted to seal the dispensing port when the recess is unaligned with the dispensing port, and a second sealing surface adapted to sealing the pressure relief port when the recess is aligned with the dispensing port and unseal the pressure relief port when the recess is unaligned with the dispensing port.

The inhaler preferably has a dose counter. The inhaler includes a mouthpiece for patient inhalation, a dose-metering arrangement including a pawl movable along a predetermined path during the metering of a dose of medicament to the mouthpiece by the dose-metering arrangement, and a dose counter.

In a preferred form, the dose counter includes a bobbin, a rotatable spool, and a rolled ribbon received on the bobbin, rotatable about an axis of the bobbin. The ribbon has indicia thereon successively extending between a first end of the ribbon secured to the spool and a second end of the ribbon positioned on the bobbin. The dose counter also includes teeth extending radially outwardly from the spool into the predetermined path of the pawl so that the spool is rotated by the pawl and the ribbon advanced onto the spool during the metering of a dose to the mouthpiece.

The preferred inhaler includes a simple, accurate and consistent mechanical dose metering system that dispenses dry powdered medicament in discrete amounts or doses for patient inhalation, a reservoir pressure system that ensures consistently dispensed doses, and a dose counter indicating the number of doses remaining in the inhaler.

With reference to the drawings, the inhaler 10 generally includes a housing 18, and an assembly 12 received in the housing (see FIG. 2). The housing 18 includes a case 20 having an open end 22 and a mouthpiece 24 for patient inhalation, a cap 26 secured to and closing the open end 22 of the case 20, and a cover 28 pivotally mounted to the case 20 for covering the mouthpiece 24 (see FIGS. 1, 2 and 9). The housing 18 is preferably manufactured from a plastic such as polypropylene, acetal or moulded polystyrene, but may be manufactured from metal or another suitable material.

The internal assembly 12 includes a reservoir 14 for containing dry powered medicament in bulk form, a deagglomerator 10' that breaks down the medicament between a delivery passageway 34 and the mouthpiece 24, and a spacer 38 connecting the reservoir to the deagglomerator.

The reservoir 14 is generally made up of a collapsible bellows 40 and a hopper 42 having an dispenser port 44 (see FIGS. 2-5 and 7-8) for dispensing medicament upon the bellows 40 being at least partially collapsed to reduce the internal volume of the reservoir.

The hopper 42 is for holding the dry powder medicament in bulk form and has an open end 46 closed by the flexible accordion-like bellows 40 in a substantially air-tight manner.

Figures 7, 8:
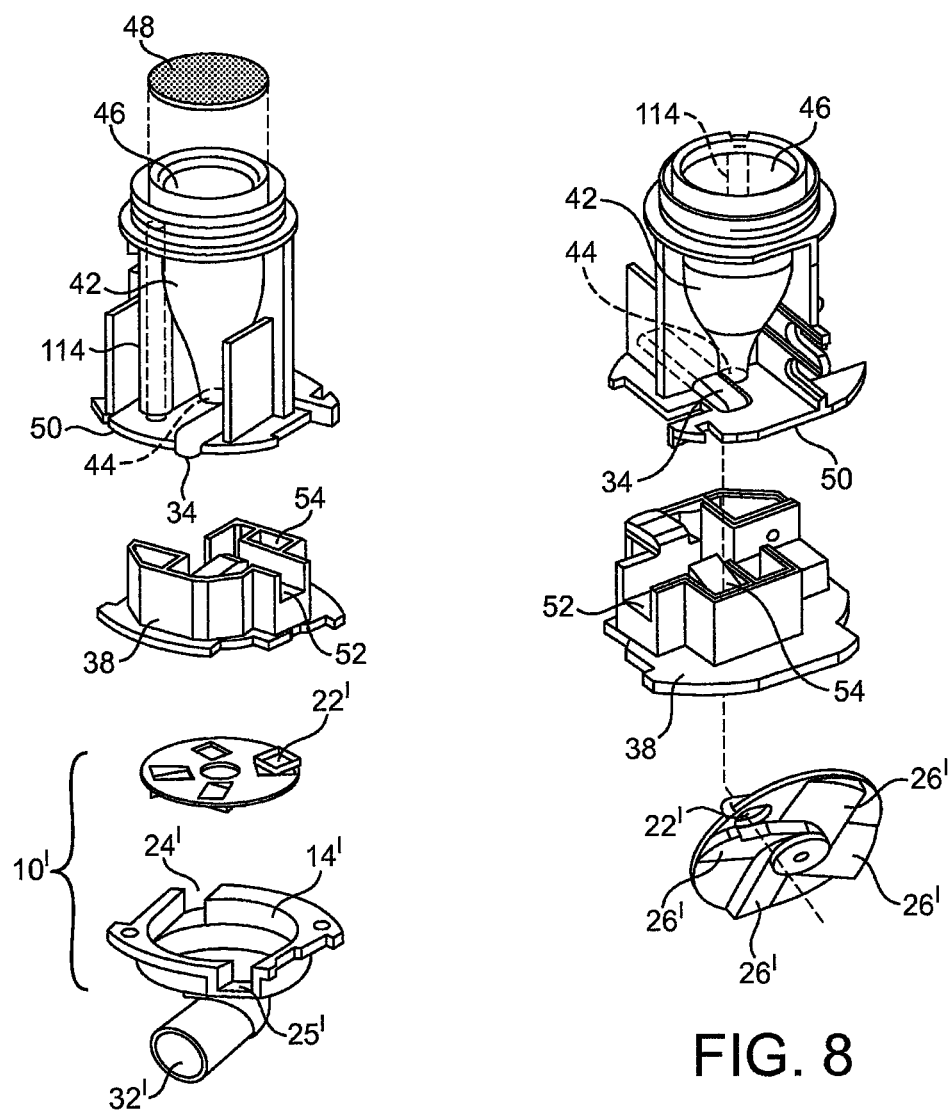
FIG. 7 is an exploded first side isometric view of a hopper and a deagglomerator of the inhaler of FIG. 1.
FIG. 8 is an exploded second side isometric view of the hopper and a swirl chamber roof of the deagglomerator of the inhaler of FIG. 1.

An air filter 48 covers the open end 46 of the hopper 42 and prevents dry powder medicament from leaking from the hopper 42 (see FIG. 7).

A base 50 of the hopper 42 is secured to a spacer 38, which is in turn secured to the deagglomerator 10' (see FIGS. 3-5 and 7-8). The hopper 42, the spacer 38, and the deagglomerator 10' are preferably manufactured from a plastic such as polypropylene, acetal or moulded polystyrene, but may be manufactured from metal or another suitable material.

The hopper 42, the spacer 38 and the deagglomerator 10' are connected in a manner that provides an air tight seal between the parts. For this purpose heat or cold sealing, laser welding or ultrasonic welding could be used, for example.

The spacer 38 and the hopper 42 together define the medicament delivery passageway 34, which preferably includes a venturi 36 (see FIG. 16) for creating an entraining air flow. The spacer 38 defines a slide channel 52 communicating with the dispenser port 44 of the hopper 42, and a chimney 54 providing fluid communication between the medicament delivery passageway 34 and a supply port 22' of the deagglomerator 10' (see FIGS. 7 and 8). The slide channel 52 extends generally normal with respect to the axis "A" of the inhaler 10.

The deagglomerator 10' breaks down agglomerates of dry powder medicament before the dry powder leaves the inhaler 10 through the mouthpiece 24.

Referring to FIGS. 17 to 22, the deagglomerator 10' breaks down agglomerates of medicament, or medicament and carrier, before inhalation of the medicament by a patient.

In general, the deagglomerator 10' includes an inner wall 12' defining a swirl chamber 14' extending along an axis A' from a first end 18' to a second end 20'. The swirl chamber 14' includes circular cross-sectional areas arranged transverse to the axis A', that decrease from the first end 18' to the second end 20' of the swirl chamber 14', such that any air flow traveling from the first end of the swirl chamber to the second end will be constricted and at least in part collide with the inner wall 12' of the chamber.

Preferably, the cross-sectional areas of the swirl chamber 14' decrease monotonically. In addition, the inner wall 12' is preferably convex, i.e., arches inwardly towards the axis A', as shown best in FIG. 22.

As shown in FIGS. 17, 19 and 22, the deagglomerator 10' also includes a dry powder supply port 22' in the first end 18' of the swirl chamber 14' for providing fluid communication between a dry powder delivery passageway of an inhaler and the first end 18' of the swirl chamber 14'. Preferably, the dry powder supply port 22' faces in a direction substantially parallel with the axis A' such that an air flow, illustrated by arrow 1' in FIG. 22, entering the chamber 14' through the supply port 22' is at least initially directed parallel with respect to the axis A' of the chamber.

Referring to FIGS. 17 to 22, the deagglomerator 10' additionally includes at least one inlet port 24' in the inner wall 12' of the swirl chamber 14' adjacent to or near the first end 18' of the chamber providing fluid communication between a region exterior to the deagglomerator and the first end 18' of the swirl chamber 14'. Preferably, the at least one inlet port comprises two diametrically opposed inlet ports 24', 25' that extend in a direction substantially transverse to the axis A' and substantially tangential to the circular cross-section of the swirl chamber 14'. As a result, air flows, illustrated by arrows 2' and 3' in FIGS. 17 and 21, entering the chamber 14' through the inlet ports are at least initially directed transverse with respect to the axis A' of the chamber and collide with the air flow 1' entering through the supply port 22' to create turbulence. The combined air flows, illustrated by arrow 4' in FIGS. 21 and 22, then collide with the inner wall 12' of the chamber 14', form a vortex, and create additional turbulence as they move towards the second end 20' of the chamber.

Referring to FIGS. 17-19 and 22, the deagglomerator 10' includes vanes 26' at the first end 18' of the swirl chamber 14' extending at least in part radially outwardly from the axis A' of the chamber. Each of the vanes 26' has an oblique surface 28' facing at least in part in a direction transverse to the axis A' of the chamber. The vanes 26' are sized such that at least a portion 4A' of the combined air flows 4' collide with the oblique surfaces 28', as shown in FIG. 22. Preferably, the vanes comprise four vanes 26', each extending between a hub 30' aligned with the axis A' and the wall 12' of the swirl chamber 14'.

As shown in FIGS. 17 to 22, the deagglomerator 10' further includes an outlet port 32' providing fluid communication between the second end 20' of the swirl chamber 14' and a region exterior to the deagglomerator. A breath-induced low pressure at the outlet port 32' causes the air flow 1' through the supply port 22' and the air flows 2',3' through the inlet ports and draws the combined air flow 4' through the swirl chamber 14'. The combined air flow 4' then exits the deagglomerator through the outlet port 32'. Preferably the outlet port 32' extends substantially transverse to the axis A', such that the air flow 4' will collide with an inner wall of the outlet port 32' and create further turbulence.

During use of the deagglomerator 10' in combination with the inhaler, patient inhalation at the outlet port 32' causes air flows 1',2',3' to enter through, respectively, the dry powder supply port 22' and the inlet ports. Although not shown, the air flow 1' through the supply port 22' entrains the dry powder into the swirl chamber 14'. The air flow 1' and entrained dry powder are directed by the supply port 22' into the chamber in a longitudinal direction, while the air flows 2',3' from the inlet ports are directed in a transverse direction, such that the air flows collide and substantial combine.

A portion of the combined air flow 4' and the entrained dry powder then collide with the oblique surfaces 28' of the vanes 26' causing particles and any agglomerates of the dry powder to impact against the oblique surfaces and collide with each other. The geometry of the swirl chamber 14' causes the combined air flow 4' and the entrained dry powder to follow a turbulent, spiral path, or vortex, through the chamber. As will be appreciated, the decreasing cross-sections of the swirl chamber 14' continuously changes the direction and increases the velocity of the spiralling combined air flow 4' and entrained dry powder. Thus, particles and any agglomerates of the dry powder constantly impact against the wall 12' of the swirl chamber 14' and collide with each other, resulting in a mutual grinding or shattering action between the particles and agglomerates. In addition, particles and agglomerates deflected off the oblique surfaces 28' of the vanes 26' cause further impacts and collisions.

Upon exiting the swirl chamber 14', the direction of the combined air flow 4 and the entrained dry powder is again changed to a transverse direction with respect to the axis A', through the outlet port 32'. The combined air flow 4' and the entrained dry powder retain a swirl component of the flow, such that the air flow 4' and the entrained dry powder spirally swirls through the outlet port 32'. The swirling flow causes additional impacts in the outlet port 32' so as to result in further breaking up of any remaining agglomerates prior to being inhaled by a patient.

As shown in FIGS. 17 to 22, the deagglomerator is preferably assembled from two pieces: a cup-like base 40' and a cover 42'. The base 40' and the cover 42' are connected to form the swirl chamber 14'. The cup-like base 40' includes the wall 12' and the second end 20' of the chamber and defines the outlet port 32'. The base 40' also includes the inlet ports of the swirl chamber 14'. The cover 42' forms the vanes 26' and defines the supply port 22'.

The base 40' and the cover 42' of the deagglomerator are preferably manufactured from a plastic such as polypropylene, acetal or moulded polystyrene, but may be manufactured from metal or another suitable material. Preferably, the cover 42' includes an anti-static additive, so that dry powder will not cling to the vanes 26'. The base 40' and the cover 42' are then connected in a manner that provides an air tight seal between the parts. For this purpose heat or cold sealing, laser welding or ultra-sonic welding could be used, for example.

Although the inhaler 10 is shown with a particular deagglomerator 10', the inhaler 10 is not limited to use with the deagglomerator shown and can be used with other types of deagglomerators or a simple swirl chamber.

Figure 1:
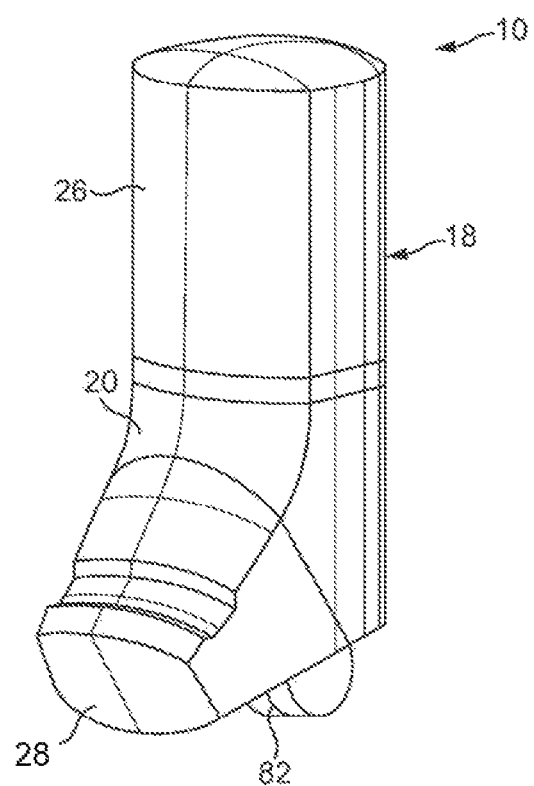
FIG. 1 is a first side isometric view of a dry powder inhaler according to a preferred embodiment.
Figure 2:
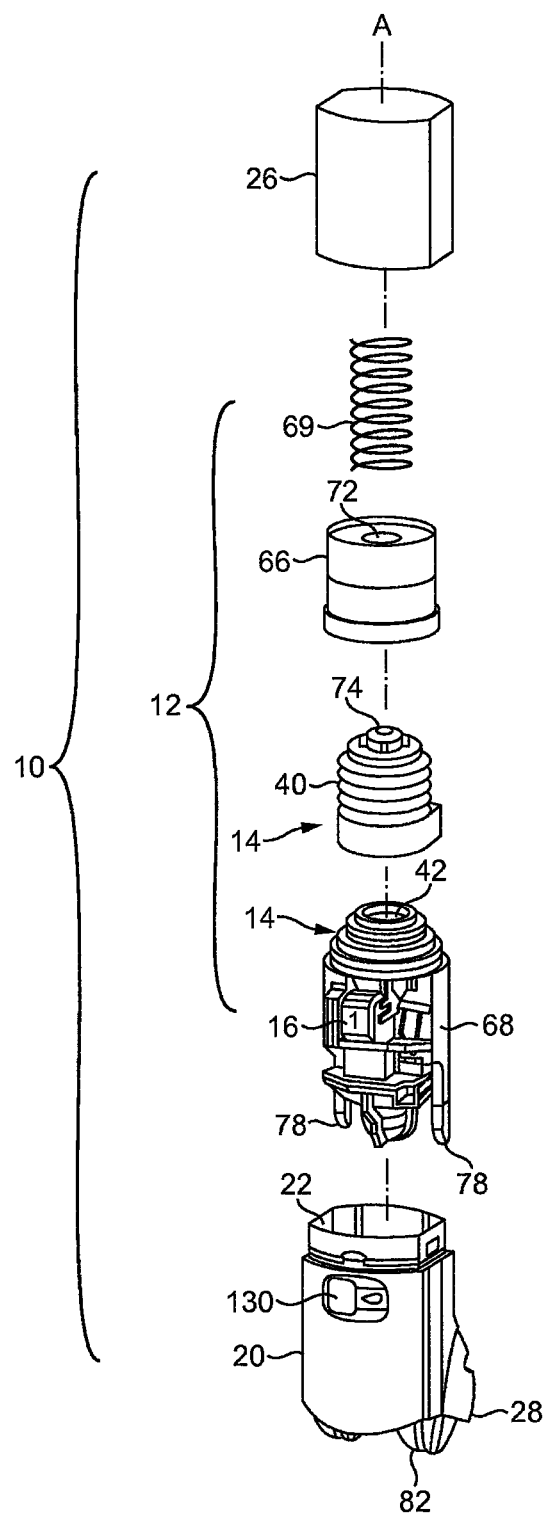
FIG. 2 is an exploded, second side isometric view of the inhaler of FIG. 1.
Figure 3:
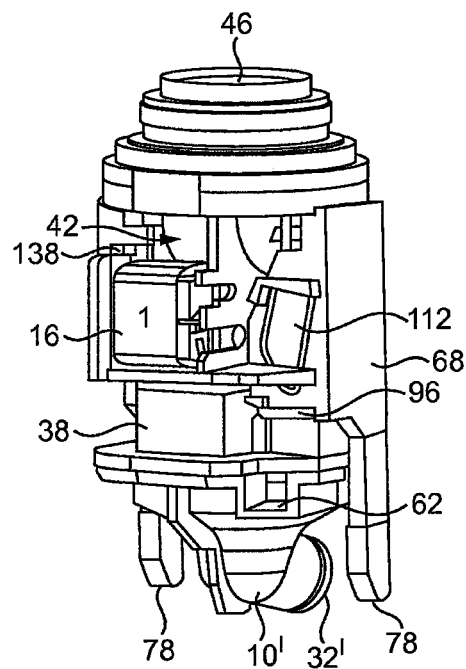
FIG. 3 is a second side isometric view of a main assembly of the inhaler of FIG. 1.
Figure 4:
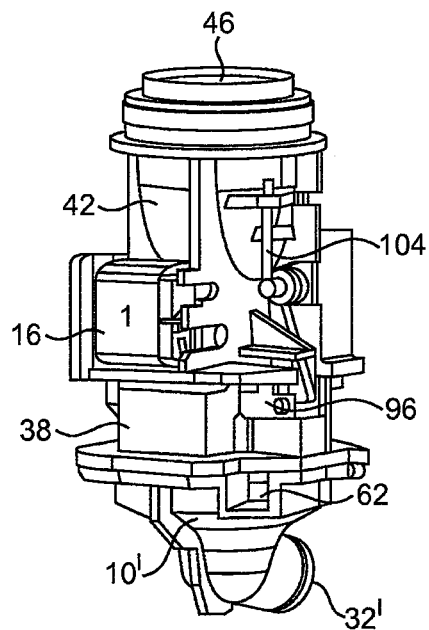
FIG. 4 is a second side isometric view of the main assembly of the inhaler of FIG. 1, shown with a yoke removed.

The dose metering system includes a first yoke 66 and a second yoke 68 mounted on the internal assembly 12 within the housing 18, and movable in a linear direction parallel with an axis "A" of the inhaler 10 (see FIG. 2). An actuation spring 69 is positioned between the cap 26 of the housing 18 and the first yoke 66 for biasing the yokes in a first direction towards the mouthpiece 24. In particular, the actuation spring 69 biases the first yoke 66 against the bellows 40 and the second yoke 68 against cams 70 mounted on the mouthpiece cover 28 (see FIG. 9).

Figure 9:
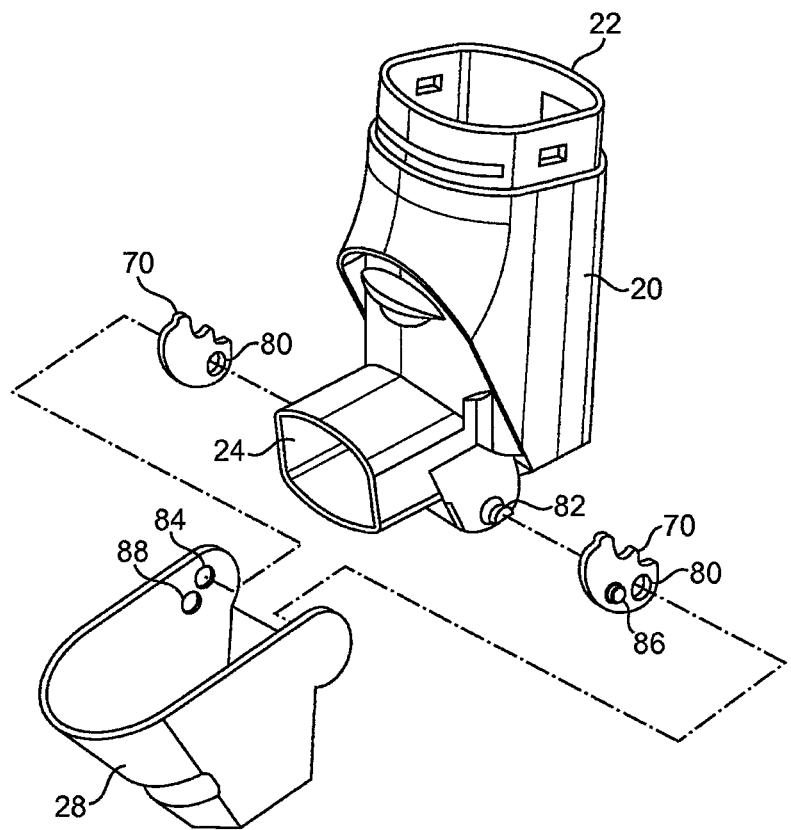
FIG. 9 is an exploded first side isometric view of a case, cams and a mouthpiece cover of the inhaler of FIG. 1.
Figure 10:
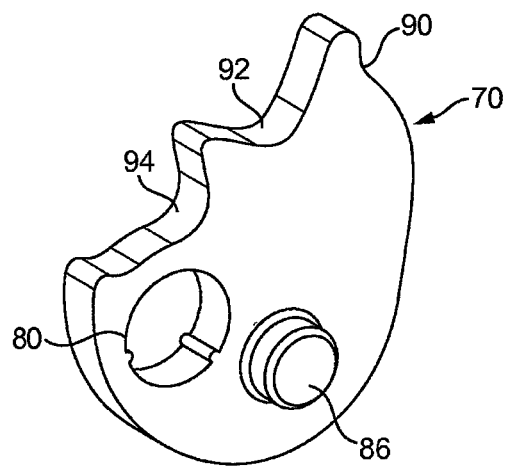
FIG. 10 is an enlarged side isometric view of one of the cams of the inhaler of FIG. 1.

The first yoke 66 includes an opening 72 that receives and retains a crown 74 of the bellows 40 such that the first yoke 66 pulls and expands the bellows 40 when moved towards the cap 26, i.e., against the actuation spring 69 (see FIG. 2). The second yoke 68 includes a belt 76, which receives the first yoke 66, and two cam followers 78 extending from the belt in a direction opposite the first yoke 66 (see FIGS. 3, 11 and 12), towards the cams 70 of the mouthpiece cover 28 (FIGS. 9,10).

The dose metering system also includes the two cams 70 mounted on the mouthpiece cover 28 (see FIGS. 9 and 10), and movable with the cover 28 between open and closed positions. The cams 70 each include an opening 80 for allowing outwardly extending hinges 82 of the case 20 to pass therethrough and be received in first recesses 84 of the cover 28. The cams 70 also include bosses 86 extending outwardly and received in second recesses 88 of the cover 28, such that the cover 28 pivots about the hinges 82 and the cams 70 move with the cover 28 about the hinges.

Each cam 70 also includes first, second and third cam surfaces 90,92,94, and the cam followers 78 of the second yoke 68 are biased against the cam surfaces by the actuation spring 69. The cam surfaces 90,92,94 are arranged such that cam followers 78 successively engage the first cam surfaces 90 when the cover 28 is closed, the second cam surfaces 92 when the cover 28 is partially opened, and the third cam surfaces 94 when the cover 28 is fully opened. The first cam surfaces 90 are spaced further from the hinges 82 than the second and the third cam surfaces, while the second cam surfaces 92 are spaced further from the hinges 82 than the third cam surfaces 94. The cams 70, therefore, allow the yokes 66,68 to be moved by the actuation spring 69 parallel with the axis "A" of the inhaler 10 in the first direction (towards the mouthpiece 24) through first, second and third positions as the cover 28 is opened. The cams 70 also push the yokes 66, 68 in a second direction parallel with the axis "A" (against the actuation spring 69 and towards the cap 26 of the housing 18) through the third, the second and the first positions as the cover 28 is closed.

The dose metering system further includes a cup assembly 96 movable between the dispenser port 44 of the reservoir 14 and the delivery passageway 34. The cup assembly 96 includes a medicament cup 98 mounted in a sled 100 slidably received in the slide channel 52 of the spacer 38 below the hopper 42 (see FIGS. 5 and 6). The medicament cup 98 includes a recess 102 adapted to receive medicament from the dispenser port 44 of the reservoir 14 and sized to hold a predetermined dose of dry powdered medicament when filled. The cup sled 100 is biased along the slide channel 52 from the dispenser port 44 of the hopper 42 towards the delivery passageway 34 by a cup spring 104, which is secured on the hopper 42 (see FIGS. 4 and 5).

Figure 5:
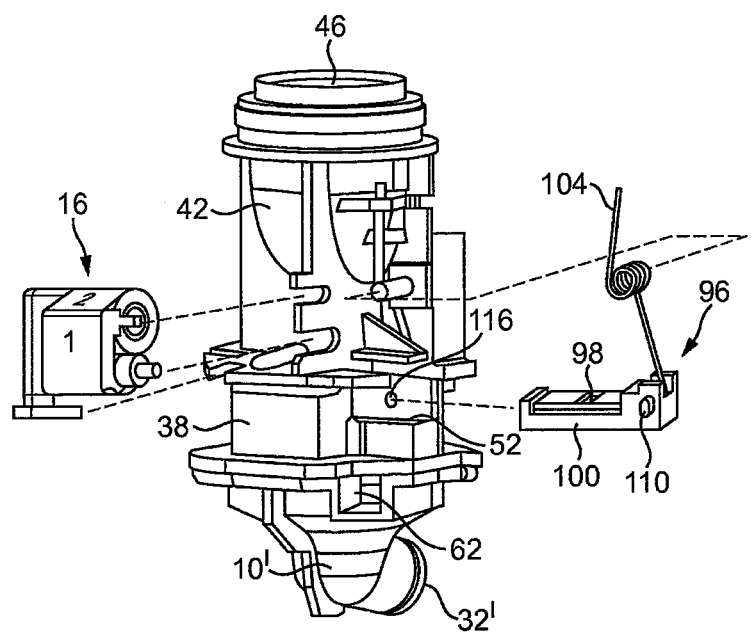
FIG. 5 is an exploded first side isometric view of the main assembly of the inhaler of FIG. 1.

The dose metering system also includes a ratchet 106 and a push bar 108 on one of the cam followers 78 of the second yoke 68 that engage a boss 110 of the cup sled 100 (see FIGS. 5,11 and 12). The ratchet 106 is mounted on a flexible flap 112 and is shaped to allow the boss 110 of the sled 100 to depress and pass over the ratchet 106, when the boss 110 is engaged by the push bar 108. Operation of the dose metering system is discussed below.

The reservoir pressure system includes a pressure relief conduit 114 in fluid communication with the interior of the reservoir 14 (see FIGS. 7 and 8), and a pressure relief port 116 in a wall of the slide channel 52 (see FIGS. 5 and 8) providing fluid communication with the pressure relief conduit 114 of the hopper 42.

Figure 6:
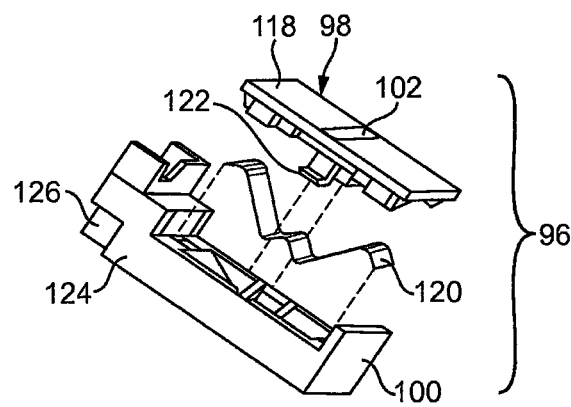
FIG. 6 is an exploded enlarged isometric view of a medicament cup of the inhaler of FIG. 1.

The medicament cup assembly 96 includes a first sealing surface 118 adapted to seal the dispenser port 44 upon the cup assembly being moved to the delivery passageway 34 (see FIGS. 5 and 6). A sealing spring 120 is provided between the sled 100 and the cup 98 for biasing the medicament cup 98 against a bottom surface of the hopper 42 to seal the dispenser port 44 of the reservoir 14. The cup 98 includes clips 122 that allow the cup to be biased against the reservoir, yet retain the cup in the sled 100.

The sled 100 includes a second sealing surface 124 adapted to seal the pressure relief port 116 when the recess 102 of the cup 98 is aligned with the dispenser port 44, and an indentation 126 (see FIG. 6) adapted to unseal the pressure relief port 116 when the first sealing surface 118 is aligned with the dispenser port 44. Operation of the pressure system is discussed below.

The dose counting system 16 is mounted to the hopper 42 and includes a ribbon 128, having successive numbers or other suitable indicia printed thereon, in alignment with a transparent window 130 provided in the housing 18 (see FIG. 2). The dose counting system 16 includes a rotatable bobbin 132, an indexing spool 134 rotatable in a single direction, and the ribbon 128 rolled and received on the bobbin 132 and having a first end 127 secured to the spool 134, wherein the ribbon 128 unrolls from the bobbin 132 so that the indicia is successively displayed as the spool 134 is rotated or advanced.

The spool 134 is arranged to rotate upon movement of the yokes 66,68 to effect delivery of a dose of medicament from the reservoir 14 into the delivery passageway 34, such that the number on the ribbon 128 is advanced to indicate that another dose has been dispensed by the inhaler 10. The ribbon 128 can be arranged such that the numbers, or other suitable indicia, increase or decrease upon rotation of the spool 134. For example, the ribbon 128 can be arranged such that the numbers, or other suitable indicia, decrease upon rotation of the spool 134 to indicate the number of doses remaining in the inhaler 10.

Alternatively, the ribbon 128 can be arranged such that the numbers, or other suitable indicia, increase upon rotation of the spool 134 to indicate the number of doses dispensed by the inhaler 10.

The indexing spool 134 preferably includes radially extending teeth 136, which are engaged by a pawl 138 extending from one of the cam followers 78 (see FIGS. 3 and 11) of the second yoke 68 upon movement of the yoke to rotate, or advance, the indexing spool 134. More particularly, the pawl 138 is shaped and arranged such that it engages the teeth 136 and advances the indexing spool 134 only upon the mouthpiece 24 cover 28 being closed and the yokes 66,68 moved back towards the cap 26 of the housing 18.

Figure 14:
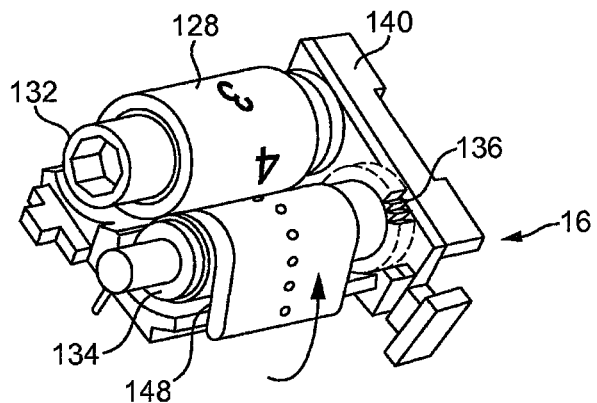
FIG. 14 is an enlarged isometric view of a dose counter of the inhaler of FIG. 1.
Figure 15:
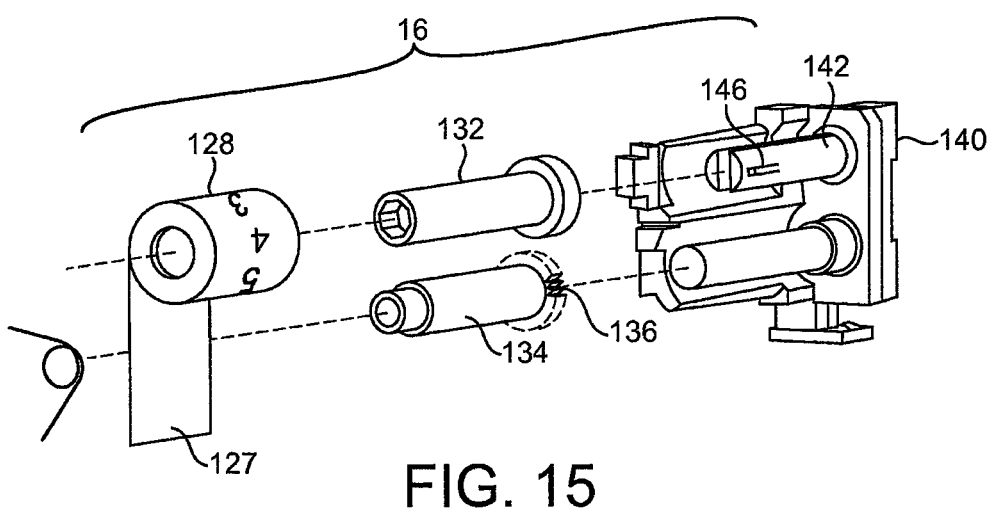
FIG. 15 is an exploded enlarged isometric view of the dose counter of the inhaler of FIG. 1.

The dose counting system 16 also includes a chassis 140 that secures the dose counting system to the hopper 42 and includes shafts 142,144 for receiving the bobbin 132 and the indexing spool 134. The bobbin shaft 142 is preferably forked and includes radial nubs 146 for creating a resilient resistance to rotation of the bobbin 132 on the shaft 142. A clutch spring 148 is received on the end of the indexing spool 134 and locked to the chassis 140 to allow rotation of the spool 134 in only a single direction (anticlockwise as shown in FIG. 14). Operation of the dose counting system 16 is discussed below.

FIG. 13 illustrates the relative movements of the boss 110 of the cup sled 100, and the ratchet 106 and the push bar 108 of the second yoke 68 as the mouthpiece cover 28 is opened and closed. In the first position of the yokes 66,68 (wherein the cover 28 is closed and the cam followers 78 are in contact with the first cam surfaces 90 of the cams 70), the ratchet 106 prevents the cup spring 104 from moving the cup sled 100 to the delivery passageway 34. The dose metering system is arranged such that when the yokes are in the first position, the recess 102 of the medicament cup 98 is directly aligned with the dispenser port 44 of the reservoir 14 and the pressure relief port 116 of the spacer 38 is sealed by the second sealing surface 124 of the cup sled 100.

Upon the cover 28 being partially opened such that the second cam surfaces 92 of the cams 70 engage the cam followers 78, the actuator spring 69 is allowed to move the yokes 66,68 linearly towards the mouthpiece 24 to the second position and partially collapse the bellows 40 of the medicament reservoir 14. The partially collapsed bellows 40 pressurizes the interior of the reservoir 14 and ensures medicament dispensed from the dispenser port 44 of the reservoir fills the recess 102 of the medicament cup 98 such that a predetermined dose is provided. In the second position, however, the ratchet 106 prevents the cup sled 100 from being moved to the delivery passageway 34, such that the recess 102 of the medicament cup 98 remains aligned with the dispenser port 44 of the reservoir 14 and the pressure relief port 116 of the spacer 38 remains sealed by the second sealing surface 124 of the cup assembly 96.

Upon the cover 28 being fully opened such that the third cam surfaces 94 engage the cam followers 78, the actuator spring 69 is allowed to move the yokes 66,68 further towards the mouthpiece 24 to the third position. When moved to the third position, the ratchet 106 disengages, or falls below the boss 110 of the cup sled 100 and allows the cup sled 100 to be moved by the cup spring 104, such that the filled recess 102 of the cup 98 is position in the venturi 36 of the delivery passageway 34 and the dispenser port 44 of the reservoir 14 is sealed by the first sealing surface 118 of the cup assembly 96. In addition, the pressure relief port 116 is uncovered by the indentation 126 in the side surface of the sled 100 to release pressure from the reservoir 14 and allow the bellows 40 to further collapse and accommodate the movement of the yokes 66,68 to the third position. The inhaler 10 is then ready for inhalation by a patient of the dose of medicament placed in the delivery passageway 34.

Figure 16:
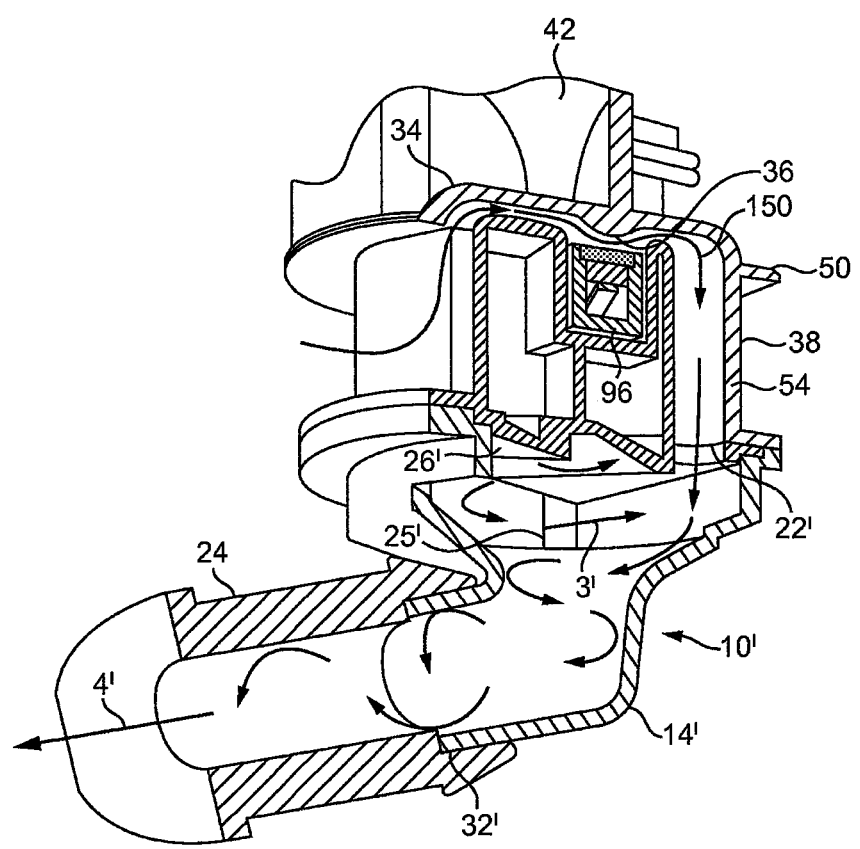
FIG. 16 is an enlarged isometric view, partially in section, of a portion of the inhaler of FIG. 1 illustrating medicament inhalation through the inhaler.
Figure 17:
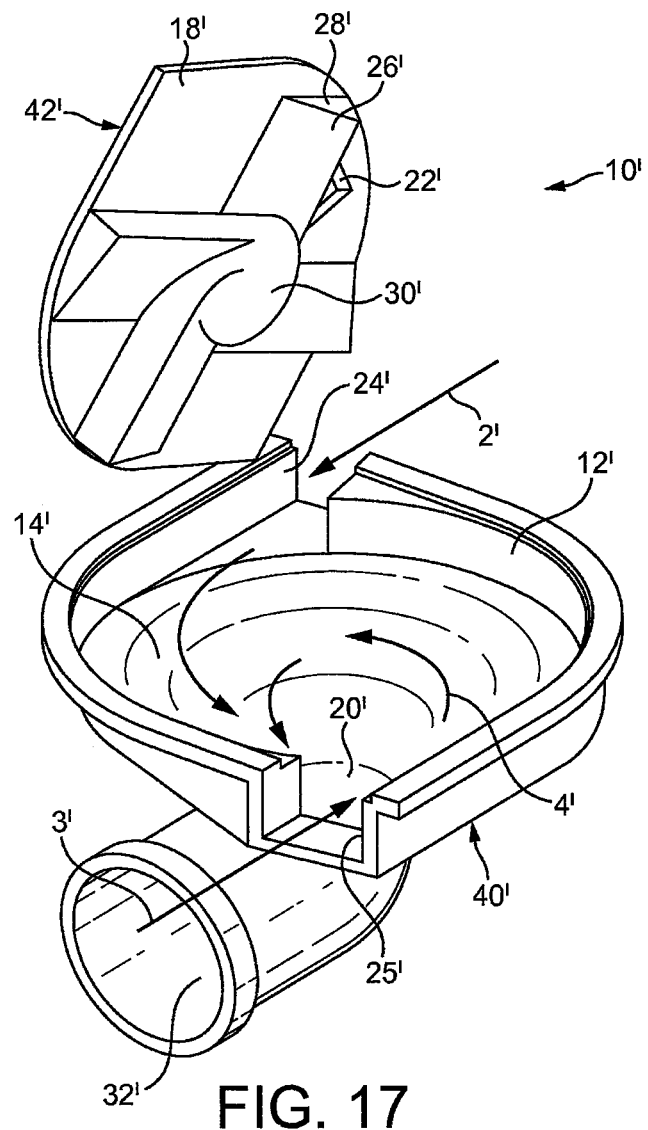
FIG. 17 is an exploded isometric view of a deagglomerator according to the present disclosure.
Figure 21:
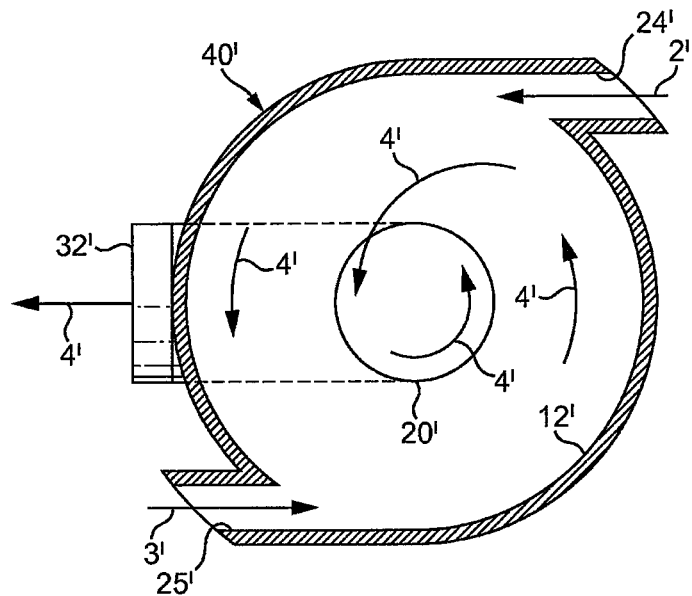
FIG. 21 is a sectional view of the deagglomerator of FIG. 17 taken along line 5'-5' of FIG. 18.
Figure 22:
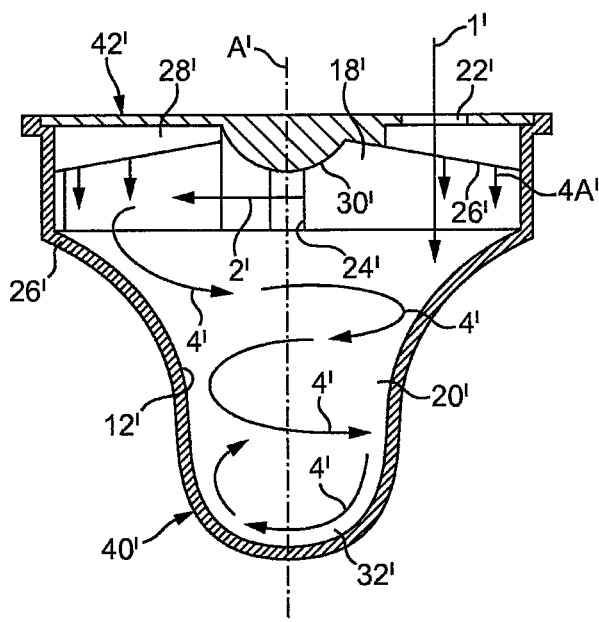
FIG. 22 is a sectional view of the deagglomerator of FIG. 17 taken along line 6'-6' of FIG. 19.

As shown in FIG. 16, a breath-induced air stream 4' diverted through the delivery passageway 34 passes through the venturi 36, entrains the medicament and carries the medicament into the deagglomerator 10' of the inhaler 10. Two other breath-induced air streams 2', 3' (only one shown) enter the deagglomerator 10' through the diametrically opposed inlet ports 24', 25' and combine with the medicament entrained air stream 150 from the delivery passageway 34. The combined flows 4' and entrained dry powder medicament then travel to the outlet port 32' of the deagglomerator and pass through the mouthpiece 24 for patient inhalation.

Once inhalation is completed, the mouthpiece cover 28 can be closed. When the cover 28 is closed, the trigger cams 70 force the yokes 66,68 upwardly such that the first yoke 66 expands the bellows 40, and the pawl 138 of the second yoke 68 advances the indexing spool 134 of the dose counting system 16 to provide a visual indication of a dose having been dispensed. In addition, the cup assembly 96 is forced back to the first position by the pusher bar 108 of the upwardly moving second yoke 68 (see FIG. 13) such that the boss 110 of the cup sled 100 is engaged and retained by the ratchet 106 of the second yoke 68.

A suitable inhaler for working the present invention is the Spiromax® DPI available from Teva Pharmaceuticals.

The medicament used in the inhaler of the present invention comprises a mixture of micronised budesonide, micronised formoterol fumarate and a lactose carrier. Micronising may be performed by any suitable technique known in the art, e.g. jet milling.

The medicament contains budesonide. It is preferable that substantially all of the particles of budesonide are less than 10 µm in size. This is to ensure that the particles are effectively entrained in the air stream and deposited in the lower lung, which is the site of action. Preferably, the particle size distribution of the budesonide is d10<1 µm, d50=<5 µm, d90=<10 µm and NLT 99%<10 µm; more preferably, the particle size distribution of the budesonide is d10<1 µm, d50=1-3 µm, d90=3-6 µm and NLT 99%<10 µm.

The delivered dose of budesonide (the amount actually delivered to the patient) is preferably 50-500 µg per actuation, with specific examples being 80, 160 and 320 µg per actuation. The inhaler of the present invention provides a delivered dose uniformity for budesonide of ±15%.

The medicament also contains formoterol fumarate. It is preferable that substantially all of the particles of formoterol fumarate are less than 10 µm in size. This is also to ensure that the particles are effectively entrained in the air stream and deposited in the lower lung, which is the site of action. Preferably, the particle size distribution of the formoterol fumarate is d10<1 µm, d50=<5 µm, d90=<10 µm and NLT 99%<10 µm; more preferably, the particle size distribution of the formoterol fumarate is d10<1 µm, d50=1-3 µm, d90=3.5-6 µm and NLT 99%<10 µm.

The delivered dose of formoterol fumarate (the "labeled" quantity), as base, is preferably 1-20 µg per actuation, with specific examples being 4.5 and 9 µg per actuation. The doses are based on the amount of formoterol present (i.e. the amount is calculated without including contribution to the mass of the counterion). The inhaler of the present invention provides a delivered dose uniformity for formoterol of ±15%.

Particularly preferred delivered doses of budesonide/formoterol in μg are 80/4.5, 160/4.5 and 320/9.

The delivered dose of the active agent is measured as per the USP <601>, using the following method. A vacuum pump (MSP HCP-5) is connected to a regulator (Copley TPK 2000), which is used for adjusting the required drop pressure $P_1$ in a DUSA sampling tube (Dosage Unit Sampling Apparatus, Copley). The inhaler is inserted into a mouthpiece adaptor, ensuring an airtight seal. $P_1$ is adjusted to a pressure drop of 4.0 KPa (3.95-4.04 KPa) for the purposes of sample testing. After actuation of the inhaler, the DUSA is removed and the filter paper pushed inside with the help of a transfer pipette. Using a known amount of solvent (acetonitrile:methanol:water (40:40:20)), the mouthpiece adaptor is rinsed into the DUSA. The DUSA is shaken to dissolve fully the sample. A portion of the sample solution is transferred into a 5 mL syringe fitted with Acrodisc PSF 0.45 μm filter. The first few drops from the filter are discarded and the filtered solution is transferred into a UPLC vial. A standard UPLC technique is then used to determine the amount of active agent delivered into the DUSA. The delivered doses of the inhaler are collected at the beginning, middle and end of inhaler life typically on three different days.

The lactose carrier has a particle size distribution of d10=20-65 μm, d50=80-120 μm, d90=130-180 μm and <10 μm=<10%. Preferably, the particle size distribution of the lactose is d10=20-65 μm, d50=80-120 μm, d90=130-180 μm and <10 μm=<6%. The lactose is preferably lactose monohydrate (for example, α-lactose monohydrate) and may be prepared by standard techniques, e.g. sieving.

The present inventors have shown that the combination of the device features, particularly the active metering from a reservoir and the cyclone chamber, and the particle size distribution of the lactose combine to provide a surprisingly uniform delivered dose. The present invention provides surprisingly improved uniform delivered dose over previously available inhaler and formulation combinations. This contributes to more consistent and reliable treatment of patients. Further surprisingly, the inhaler of the present invention has been shown to provide uniform delivered dose across a number of different flow rates. Thus, the uniform delivered dose may be obtained regardless of flow rate and thus regardless of disease severity in the patient using the device.

Indeed, a problem solved by the present invention is the need to provide consistent and reliable delivery of budesonide/formoterol to a patient in need thereof across a range of different flow rates. Generally, the more severe the patient's respiratory disease the lower the flow rate they are able to produce on inhalation. Poor delivered dose uniformity provided by prior art inhaler/formulation combination may lead to missed or inadequate dosage. This is a particular problem when the inhaler is used as a rescue or as needed medicament but is also a problem when used as a daily medicament.

Yet further, the inventors have shown that the present invention surprisingly provides uniform delivered dose independent of device orientation. Thus, the inhaler is effective at providing adequate dosing whether the patient is standing, sitting or lying down, for example.

The present invention also provides the inhaler of any aspect and embodiment of the invention for use in treating a respiratory disease. In particular, the respiratory disease may be asthma or chronic obstructive pulmonary disease (COPD).

In any aspect of the invention, it is envisaged that the asthma may be any severity of asthma, for example the asthma may be mild, mild to moderate, moderate, moderate to severe, or severe asthma. Such asthma may be classified as GINA stage 1, 2, 3 or 4 according to the Global Initiative for Asthma (GINA) guidelines, as would be understood by a person of skill in the art.

The particle size distributions of the active ingredients and lactose provided herein may be measured by laser diffraction as a dry dispersion, e.g. in air, such as with a Sympatec HELOS/BF equipped with a RODOS disperser.

The present invention also provides a pharmaceutical composition for inhalation, wherein the composition comprises micronised formoterol fumarate, micronised budesonide and a lactose carrier, the lactose carrier having a particle size distribution of d10=20-65 μm, d50=80-120 μm, d90=130-180 μm and <10 μm=<10%. The particle size distribution of the lactose may be d10=20-65 μm, d50=80-120 μm, d90=130-180 μm and <10 μm=<6%. The particle size of the budesonide may be d10<1 μm, d50=<5 μm, d90=<10 μm and NLT 99%<10 μm. The particle size of the formoterol fumarate may be d10<1 μm, d50=<5 μm, d90=<10 μm and NLT 99%<10 μm.

The invention also includes the pharmaceutical composition according to the preceding aspect for use in treating a respiratory disease, such as asthma or COPD.

The present invention will now be described with reference to the examples, which are not intended to be limiting.

EXAMPLES

Example 1

Three formulations of Budesonide/Formoterol (BF) Spiromax (Teva Pharmaceuticals) were prepared: low strength (120 inhalations, each delivering 80 μg budesonide and 4.5 μg formoterol), middle strength (120 inhalations, 160 μg budesonide and 4.5 μg formoterol per inhalation), and high strength (60 inhalations, 320 μg budesonide and 9 μg formoterol per inhalation). Two studies were performed: the first was a laboratory study designed to measure the uniformity of delivered dose (UDD) throughout the lifetime of the BF Spiromax inhaler (as an indication of dose consistency) from the first dose until the last labeled dose. The second study investigated the dose consistency (as UDD) of BF Spiromax under conditions simulating real-world inhaler handling and dosing regimens.

The compositions of the three strengths of BF Spiromax per container are set out in Tables 1-3.

TABLE 1

Composition per container of BF Spiromax 80/4.5 μg 120 inhalation product

| Material | Weight | Function | Quality Standard |
|---|---|---|---|
| Budesonide (micronised) | 12.0 mg | Drug substance | Ph. Eur. |
| Formoterol fumarate dihydrate (micronised) | 0.645 mg | Drug substance | Ph. Eur. |
| Lactose monohydrate | 1.487 g | Excipient | Ph. Eur. |
| Target fill weight per device | 1.500 g | | |

TABLE 2

Composition per Container of BF Spiromax 160/4.5 µg 120 inhalation product

| Material | Weight | Function | Quality Standard |
|---|---|---|---|
| Budesonide (micronised) | 31.6 mg | Drug substance | Ph. Eur. |
| Formoterol fumarate dihydrate (micronised) | 0.914 mg | Drug substance | Ph. Eur. |
| Lactose monohydrate | 0.838 g | Excipient | Ph. Eur. |
| Target fill weight per device | 0.870 g | | |

TABLE 3

Composition per Container of BF Spiromax 320/9 µg 60 inhalation product

| Material | Weight | Function | Quality Standard |
|---|---|---|---|
| Budesonide (micronised) | 28.7 mg | Drug substance | Ph. Eur. |
| Formoterol fumarate dihydrate (micronised) | 0.870 mg | Drug substance | Ph. Eur. |
| Lactose monohydrate | 0.840 g | Excipient | Ph. Eur. |
| Target fill weight per device | 0.870 g | | |

Study 1, UDD Over Product Lifetime

BF Spiromax devices were used according to the information for patients with respect to storage, orientation, and minimum dosing interval. Three different BF Spiromax inhalers were investigated: low strength; middle strength; and high strength. The devices were not cleaned throughout their lifetime (from beginning of life ("BOL") to end of life ("EOL")). Inhalers were selected from three batches of low strength BF Spiromax (n=42), three batches of the middle strength product (n=42) and three batches of high strength BF Spiromax (n=42).

To assess UDD over the device lifetime a fixed flow rate of 62.5 L/min, representing a 4 KPa pressure drop over the device (Q) was applied to achieve an inhalation volume of 4 L. Ten doses from different stages of the BF Spiromax lifetime were collected separately using a dose uniformity sampling apparatus (DUSA). Three doses were collected from the first discharges of the device (BOL), four doses were taken midway through the inhaler lifetime (middle of life ("MOL")) and three doses from the end of the inhaler's lifetime including the last labeled dose (EOL). After 4 L of air had been drawn through the device, the collected doses of budesonide and formoterol were recovered and analysed using validated high performance liquid chromatography (HPLC).

Study 2, Real-World Simulations

Real-world conditions were simulated by analysts carrying inhalers with them during working day hours, dispensing doses according to specified schemes and cleaning the inhaler mouthpiece weekly with a dry cloth in accordance with the patient leaflet. Five different simulation schemes were designed to test inhalers up to their last labeled doses, as summarised in Table 4.

TABLE 4

Study simulation schemes

| Scheme | Inhaler Strength | Dosing Regimen | Duration | Number of Inhalers | UDD Assessments |
|---|---|---|---|---|---|
| A | Low | One inhalation twice daily | 72 days | 6 (3 from each of 2 batches) | Day 1-2 (3 doses) Day 36-37 (4 doses) Day 71-72 (3 doses) |
| B | Low | Four inhalations twice daily | 21 days | 6 (3 from each of 2 batches) | Day 1 (3 doses) Day 10 (4 doses) Day 21 (3 doses) |
| C | High | One inhalation twice daily | 32 days | 6 (3 from each of 2 batches) | Day 1-4 (3 doses) Day 15-18 (4 doses) Day 29-32 (3 doses) |
| D | High | Two inhalations twice daily | 16 days | 6 (3 from each of 2 batches) | Day 1 (3 doses) Day 8 (4 doses) Day 15-16 (3 doses) |
| E | Middle | One inhalation twice daily | 90 days | 9 (3 from each of 3 batches) | Day 1-2 (3 doses) Day 45-48 (4 doses) Day 87-90 (3 doses) |

Within each scheme, inhaler doses were collected for UDD analysis. For UDD assessments, doses were collected into a DUSA at a pressure drop of 4 KPa over the device. After 4 L of air were drawn through the device, collected drug substances were recovered and analysed using a validated HPLC. Results obtained from the same inhaler batches under laboratory conditions (25° C., 60% relative humidity) over a single day were used for comparison.

Results for Study 1, UDD Over Product Lifetime

Figure 23:
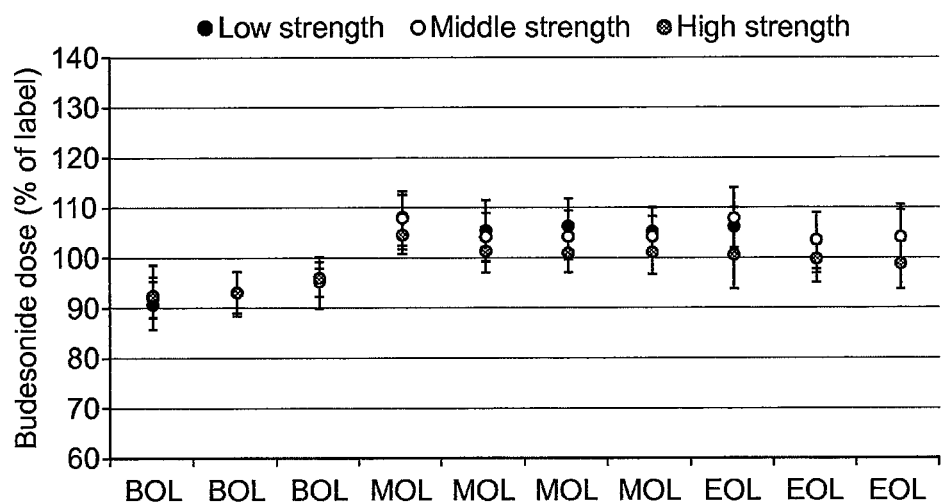
FIG. 23 shows the delivered dose (DD) of budesonide by low, middle and high strength BF Spiromax inhalers at BOL, MOL and EOL of each device (error bars represent standard deviation and data are presented as percentage of the labeled dose)

The BF Spiromax devices delivered consistent doses of budesonide and formoterol throughout their lifetime (FIGS. 23 and 24). Importantly, mean doses for the lifetime of each formulation were similar to the labeled doses (Table 5). Although there was a trend for BOL doses to be slightly lower than MOL and EOL, all doses were within ±15% of the labeled quantity (low strength doses ranged between 90.7 and 108.0% of the labeled dose for budesonide and 87.6-101.1% for formoterol. Middle strength ranges were 92.4-108.5% and 94.8-109.9%. High strength ranges were 92.7-104.8% and 96.8-110.2%).

TABLE 5

Delivered doses of budesonide and formoterol: device lifetime mean, calculated for each formulation (three doses at beginning of life, four doses at middle of life and three doses at end of life). Standard deviations are shown in parentheses.

|  | Low Strength | Middle Strength | High Strength |
|---|---|---|---|
| Budesonide, μg | 82 (5) | 163 (9) | 317 (12) |
| Formoterol, μg | 4.3 (0.3) | 4.7 (0.3) | 9.4 (0.4) |

Results for Study 2, Real-World Simulations

UDD data for budesonide and formoterol under 'real-world' conditions (expressed as delivered dose [% of labeled dose]) across simulation schemes A-E are shown in FIG. 25. For all three inhaler strengths, delivered doses were consistent throughout the lifetime. There was no difference in UDD data between single-inhalation/day and multiple-inhalation/day regimens (FIG. 25).

Example 2

Certain patients, such as children, adolescents and adults with COPD, tend to have lower peak inspiratory flow rates. It is therefore important for a device/formulation to provide a UDD over a range of flow rates. In this example, the flow rates of 40, 60 and 90 L/min were employed to represent the minimum, median and maximum flow rates achievable by all patients through the Spiromax device. Delivered dose uniformity and fine particle mass of BF Spiromax were investigated over this clinically relevant flow rate range.

The study was conducted on three batches of the low and middle strength products, containing 120 doses and of the high strength product, containing 60 doses. Three inhalers were tested for each batch at each flow rate. Ten delivered doses, three at the beginning, for in the middle and three at end of the inhaler life were collected from each inhaler separately into a dose unit sampling apparatus using 4 L air volume at the selected flow rate per the standard UDD procedure. Two APSD determinations were conducted on the inhaler used for UDD test, one at the beginning and another at the end of the inhaler life. Therefore, the mean delivered dose was calculated from a total of 30 delivered dose results and the mean FPD was calculated from a total of six sets of data (i.e. two NGIs per inhaler) for each batch tested at each flow rate.

The mean delivered dose and relative standard deviation (RSD) per batch and flow rate are presented in Tables 6-8 for low, middle and high strength BF Spiromax products, respectively. Typically, lower delivered doses are obtained at the test flow rate of 40 L/min and higher delivered doses at the test flow rate of 90 L/min. On all occasions the mean delivered dose (n=30 doses) per batch per test is well within 85-115% of the label claim for low, middle and high strength BF Spiromax products, respectively.

TABLE 6

Mean delivered dose (DD) and RSD results obtained at different flow rates for the low strength product (n = 30)

|  |  | Budesonide | | Formoterol | |
|---|---|---|---|---|---|
| Batch | Flow rate | Mean DD (μg) | RSD (%) | Mean DD (μg) | RSD (%) |
| MD0001 | 40 L/min | 76.2 | 7.0 | 4.0 | 6.9 |
|  | 60 L/min | 81.3 | 6.5 | 4.2 | 6.7 |
|  | 90 L/min | 86.4 | 3.5 | 4.6 | 5.1 |
| MD0002 | 40 L/min | 78.4 | 9.5 | 4.0 | 8.1 |
|  | 60 L/min | 83.6 | 7.1 | 4.3 | 7.1 |
|  | 90 L/min | 87.2 | 5.6 | 4.7 | 7.1 |
| MD0003 | 40 L/min | 75.0 | 7.1 | 3.8 | 6.5 |
|  | 60 L/min | 80.3 | 6.3 | 4.2 | 5.5 |
|  | 90 L/min | 83.6 | 3.8 | 4.5 | 4.7 |

TABLE 7

Mean DD and RSD results obtained at different flow rates for the middle strength product (n = 30)

|  |  | Budesonide | | Formoterol | |
|---|---|---|---|---|---|
| Batch | Flow rate | Mean DD (μg) | RSD (%) | Mean DD (μg) | RSD (%) |
| MD8001 | 40 L/min | 147.4 | 11.0 | 4.1 | 13.8 |
|  | 60 L/min | 155.7 | 6.9 | 4.4 | 7.5 |
|  | 90 L/min | 175.2 | 6.0 | 5.1 | 7.7 |
| MD8002 | 40 L/min | 157.8 | 8.0 | 4.3 | 7.9 |
|  | 60 L/min | 157.7 | 8.2 | 4.4 | 7.8 |
|  | 90 L/min | 171.3 | 3.9 | 4.9 | 5.5 |
| MD8003 | 40 L/min | 148.2 | 10.1 | 4.1 | 12.3 |
|  | 60 L/min | 164.7 | 7.1 | 4.6 | 10.4 |
|  | 90 L/min | 172.9 | 4.8 | 5.1 | 6.7 |

TABLE 8

Mean DD and RSD results obtained at different flow rates for the high strength product (n = 30)

|  |  | Budesonide | | Formoterol | |
|---|---|---|---|---|---|
| Batch | Flow rate | Mean DD (µg) | RSD (%) | Mean DD (µg) | RSD (%) |
| MD9001 | 40 L/min | 288.4 | 7.7 | 8.2 | 8.2 |
|  | 60 L/min | 313.6 | 5.8 | 9.0 | 7.7 |
|  | 90 L/min | 321.9 | 6.2 | 9.4 | 8.9 |
| MD9002 | 40 L/min | 302.7 | 6.5 | 8.8 | 6.7 |
|  | 60 L/min | 318.9 | 8.4 | 9.3 | 10.3 |
|  | 90 L/min | 321.7 | 5.7 | 9.6 | 6.8 |
| MD9003 | 40 L/min | 304.6 | 8.3 | 9.0 | 9.1 |
|  | 60 L/min | 320.2 | 5.6 | 9.4 | 6.0 |
|  | 90 L/min | 330.3 | 4.8 | 9.9 | 6.0 |

This example demonstrates the consistency of the minimum delivered dose and the fine particle mass over the range of flow rates achievable by the intended patient populations, at constant volume of 4 L. It can therefore be concluded based on this study outcome that the present BF Spiromax product is capable of delivering safe and efficacious doses at clinically relevant flow rates.

Example 3

Routine laboratory testing is conducted on inhalers when they are actuated and metered doses extracted with the inhalers being held in the upright orientation. A patient may actuate the device and inhale the dose while holding the inhaler in other orientations. A device orientation study was conducted to evaluate how the orientation during actuation or inhalation affects dose delivery from the present BF Spiromax product. Product performance was assessed in terms of UDD with the inhaler angled forwards (plus) or backwards (minus) 45° of the default upright orientation, during actuation or discharge and compared with routine test results (Control).

Three batches of the low strength and three batches of the high strength products were tested in accordance with the routine test scheme for UDD. Per batch three inhalers were tested. Waste doses were actuated and collected when the inhalers are held in the upright orientation. Tilted actuation: Actuation with device held at +45° or −45° followed by discharge into a sample collection tube in the normal upright orientation. Tilted discharge: Actuation in the normal upright orientation followed by discharge into a sample collection tube in an angled orientation of +45° or −45°. The results are shown in Table 9.

The results show that actuating the present device/formulation or inhaling the metered dose at angled orientations within 45° from upright orientation does not change the dose delivery profile compared to the inhalers actuated and metered dose inhaled in the upright orientation.

The invention claimed is:
1. A budesonide/formoterol dry powder inhaler comprising:
   a reservoir containing a dry powder medicament comprising an active ingredient and a lactose carrier, and an arrangement for delivering a metered dose of the medicament from the reservoir;
   a deagglomerator; and
   a delivery passageway for directing an inhalation-induced air flow through a mouthpiece, the delivery passageway extending to the metered dose of medicament,
   wherein the active ingredient consists of micronised formoterol fumarate and micronised budesonide, and
   the lactose carrier has a particle size distribution of d10=20-65 µm, d50=80-120 µm, d90=130-180 µm and <10 µm=<10% measured by laser diffraction as a dry dispersion.
2. The inhaler as claimed in claim 1, wherein the deagglomerator comprises:
   an inner wall defining a swirl chamber extending along an axis from a first end to a second end;
   a dry powder supply port in the first end of the swirl chamber for providing fluid communication between the delivery passageway of the inhaler and the first end of the swirl chamber;
   at least one inlet port in the inner wall of the swirl chamber adjacent to the first end of the swirl chamber providing fluid communication between a region exterior to the deagglomerator and the first end of the swirl chamber;
   an outlet port providing fluid communication between the second end of the swirl chamber and a region exterior to the deagglomerator; and
   vanes at the first end of the swirl chamber extending at least in part radially outwardly from the axis of the chamber, each of the vanes having an oblique surface facing at least in part in a direction transverse to the axis; whereby a breath-induced low pressure at the outlet port causes air flows into the swirl chamber through the dry powder supply port and the inlet port.
3. The inhaler of claim 1, wherein the reservoir is a sealed reservoir including a dispensing port, and the inhaler further comprises

TABLE 9

Overall mean delivered doses per strength obtained in different orientations of actuation or inhalation (n = 9 inhalers)

|  |  |  | Mean dose (µg) | | | RSD (%) | | |
|---|---|---|---|---|---|---|---|---|
| Component | Strength | Test | +45° | −45° | Control | +45° | −45° | Control |
| Budesonide | Low | Inhalation | 81.9 | 81.2 | 81.9 | 5.5 | 5.7 | 5.1 |
| Budesonide | Low | Actuation | 81.5 | 82.9 | 81.9 | 6.8 | 6.2 | 5.1 |
| Budesonide | High | Inhalation | 332.1 | 323.4 | 326.0 | 4.9 | 8.1 | 5.3 |
| Budesonide | High | Actuation | 328.0 | 328.0 | 326.0 | 5.1 | 5.9 | 5.3 |
| Formoterol | Low | Inhalation | 4.33 | 4.35 | 4.35 | 6.2 | 5.7 | 6.8 |
| Formoterol | Low | Actuation | 4.33 | 4.43 | 4.35 | 7.4 | 6.2 | 6.8 |
| Formoterol | High | Inhalation | 9.52 | 9.50 | 9.53 | 8.0 | 11.2 | 8.0 |
| Formoterol | High | Actuation | 9.52 | 9.54 | 9.53 | 9.1 | 7.8 | 8.0 | a channel communicating with the dispensing port and including a pressure relief port;

a conduit providing fluid communication between an interior of the sealed reservoir and the pressure relief port of the channel; and a cup assembly movably received in the channel and including, a recess adapted to receive the medicament when aligned with the dispensing port, a first sealing surface adapted to seal the dispensing port when the recess is unaligned with the dispensing port, and a second sealing surface adapted to seal the pressure relief port when the recess is aligned with the dispensing port and unseal the pressure relief port when the recess is unaligned with the dispensing port.

4. The inhaler of claim 1, wherein the particle size distribution of the lactose is d10=20-65 μm, d50=80-120 μm, d90=130-180 μm and <10 μm=<6% measured by laser diffraction as a dry dispersion.

5. The inhaler of claim 1, wherein the particle size of the budesonide is d10<1 μm, d50=<5 μm, d90=<10 μm and NLT 99%<10 μm measured by laser diffraction as a dry dispersion.

6. The inhaler of claim 1, wherein the particle size of the formoterol fumarate is d10<1 μm, d50=<5 μm, d90=<10 μm and NLT 99%<10 μm measured by laser diffraction as a dry dispersion.

7. The inhaler of claim 1, wherein the delivered dose of budesonide is 50-500 μg per actuation.

8. The inhaler of claim 1, wherein the delivered dose of formoterol is 1-20 μg per actuation.

9. The inhaler of claim 1, wherein the delivered doses of budesonide/formoterol in μg are 80/4.5, 160/4.5 or 320/9 per actuation.

10. A method of treating a respiratory disease in a patient comprising administering formoterol and budesonide to the patient using the inhaler of claim 1.

11. The method of claim 10, wherein the respiratory disease is asthma or chronic obstructive pulmonary disease.

12. The method of claim 11, wherein the asthma is mild, moderate or severe asthma classed as GINA stage 1, 2, 3 or 4.

13. A method of treating a respiratory disease in a patient comprising administering a pharmaceutical composition by inhalation, wherein the composition comprises an active ingredient and a lactose carrier, wherein the active ingredient consists of micronised formoterol fumarate and micronised budesonide, and the lactose carrier has a particle size distribution of d10=20-65 μm, d50=80-120 μm, d90=130-180 μm and <10 μm=<10% measured by laser diffraction as a dry dispersion.

* * * * *